US007828724B2

(12) United States Patent
Hosoi et al.

(10) Patent No.: US 7,828,724 B2
(45) Date of Patent: Nov. 9, 2010

(54) ENDOSCOPE INCLUDING A FLEXIBLE TUBE

(75) Inventors: Masayoshi Hosoi, Tokyo (JP); Takuji Yamada, Saitama (JP)

(73) Assignee: Hoya Corporation, Tokyo (JP)

( * ) Notice: Subject to any disclaimer, the term of this patent is extended or adjusted under 35 U.S.C. 154(b) by 860 days.

(21) Appl. No.: 11/621,644

(22) Filed: Jan. 10, 2007

(65) Prior Publication Data

US 2007/0161860 A1    Jul. 12, 2007

(30) Foreign Application Priority Data

Jan. 10, 2006  (JP)  ............................ P2006-002384
Oct. 20, 2006  (JP)  ............................ P2006-285835

(51) Int. Cl.
*A61B 1/00* (2006.01)

(52) U.S. Cl. ...................... 600/142; 141/139; 141/140; 141/128

(58) Field of Classification Search ................ 600/106, 600/114, 139–142, 146, 121, 128, 133
See application file for complete search history.

(56) References Cited

U.S. PATENT DOCUMENTS 5,271,381 A * 12/1993 Ailinger et al. ............. 600/128

7,044,906 B2     5/2006  Hosoi et al.
2002/0032371 A1 * 3/2002  Torii .......................... 600/142
2005/0020881 A1   1/2005  Hosoi et al.
2005/0061381 A1   3/2005  Hosoi et al.

FOREIGN PATENT DOCUMENTS

JP          9-24020       1/1997

OTHER PUBLICATIONS

U.S. Appl. No. 11/565,145 to Hosoi et al., which was filed on Nov. 30, 2006.
English Language Abstract of JP 9-24020.

* cited by examiner

*Primary Examiner*—Linda C Dvorak
*Assistant Examiner*—Ryan Henderson
(74) *Attorney, Agent, or Firm*—Greenblum & Bernstein P.L.C.

(57) ABSTRACT

There is provided a flexible tube for an endoscope, including a framed structure unit having a plurality of joint members rotatably coupled to each other so that the framed structure unit is able to bend freely, each joint member having a form of a short cylinder, a reticulated tube that is reticulated with thread and is formed to cover the framed structure unit, and a flexible sheath that has flexibility and is formed to cover the reticulated tube. Further, a cross section of an outer surface of the flexible sheath has a circular shape, and a cross section of an outer surface of each joint member has a non-circular shape so that a wall thickness of the flexible sheath has a thicker part in a particular direction about an axis line of the flexible tube than another part of the wall thickness of the flexible sheath.

9 Claims, 8 Drawing Sheets

ENDOSCOPE INCLUDING A FLEXIBLE TUBE

BACKGROUND OF THE INVENTION

The present invention relates to a flexible tube for an endoscope.

In general, an endoscope includes a flexible tube which is inserted into a human cavity, and the flexible tube includes a spirally-wound metal tube, a reticulated tube and a flexible sheath. The spirally-wound metal tube is covered with the reticulated tube, and further the reticulated tube is covered with the flexible sheath.

There may be a case where the spirally-wound metal tube undesirably shrinks by autoclaving which is performed after use of the endoscope. Therefore, it is desirable to enhance durability of the flexible tube against autoclaving. Japanese Patent Provisional Publication No. HEI 9-24020° A. discloses a flexible tube for an endoscope. The flexible tube in this publication uses a framed structure unit configured such that a plurality of joint members each of which has a form of a short cylinder are coupled to each other with rivets, in place of the spirally-wound metal tube. By this structure, durability with respect to autoclaving can be enhanced.

However, the flexible tube disclosed in HEI 9-24020A has a drawback that a twisting response, representing rotating motion of a tip portion of the flexible tube in response to an operation to rotate a proximal portion of the flexible tube about an axis line, and resilience, representing motion of the flexible tube getting back to a straightened state after being bent by an external force, are less than those of the flexible tube employing the spirally-wound metal tube. Therefore, usability of the flexible tube having the framed structure unit may be less than that of the flexible tube employing the spirally-wound metal tube.

SUMMARY OF THE INVENTION

The present invention is advantageous in that it provides a flexible tube for an endoscope configured to have a framed structure unit in which a plurality of joint members having a form of a short cylinder are coupled to each other to enhance durability against autoclaving, and to have excellent twisting response and resilience.

According to an aspect of the invention, there is provided a flexible tube for an endoscope. The flexible tube includes a framed structure unit having a plurality of joint members rotatably coupled to each other so that the framed structure unit is able to bend freely, each joint member having a form of a short cylinder, a reticulated tube that is reticulated with thread and is formed to cover the framed structure unit, and a flexible sheath that has flexibility and is formed to cover the reticulated tube. Further, a cross section of an outer surface of the flexible sheath has a circular shape, and a cross section of an outer surface of each joint member has a non-circular shape so that a wall thickness of the flexible sheath has a thicker part in a particular direction about an axis line of the flexible tube than another part of the wall thickness of the flexible sheath.

By virtue of the above mentioned configuration, the thickness of the flexible sheath in a particular direction about the axis line is larger than that of another direction about the axis line. Therefore, excellent twisting response and resilience can be achieved in regard to a flexible tube for an endoscope employing framed structure unit in which a plurality of joint members are rotatably coupled to each other to enhance durability against autoclaving.

In at least one aspect, each joint member is configured in such a form that a short cylinder is crushed at positions 90° apart in angle with respect to each other about the axis line so that a cross section of each joint member has a flat shape at each crushed part.

In at least one aspect, each joint member has a connection part, the plurality of joint members are coupled to each other by connecting connection parts of neighboring joint members with each other; and each joint member has the flat shape in a direction about the axis line in which the connection part is formed, when viewed as a cross section.

In at least one aspect, the cross section of the outer surface of each joint member has partially a circular shape.

In at least one aspect, each joint member is configured to have such a form that a circular short cylinder is crushed on a side of a first end portion to have an elliptical shape and is crushed on a side of a second end portion to have an elliptical shape having a direction of a major axis perpendicularly crossing a direction of a major axis of the elliptical shape formed at the first end portion. In this structure, a cross section of an intermediate part of the circular short cylinder is formed to be the circular shape.

In at least one aspect, the flexible tube is formed by extrusion molding.

According to another aspect of the invention, there is provided a flexible tube for an endoscope. The flexible tube includes a framed structure unit having a plurality of joint members rotatably coupled to each other so that the framed structure unit is able to bend freely, each joint member having a form of a short cylinder, a reticulated tube that is reticulated with thread and is formed to cover the framed structure unit, and a flexible sheath that has flexibility and is formed to cover the reticulated tube. Further, a cross section of an outer surface of the flexible sheath has a circular shape, a cross section of an outer surface of each joint member has a non-circular shape. Reinforcing material is provided in space formed between an inner surface of the flexible sheath and the outer surface of each joint member, the space in which the reinforcing material is provided is located at a portion where a distance between the outer surface of the flexible sheath and the outer surface of each joint member is larger than that of another portion in an circumferential direction of the flexible tube.

By virtue of the above mentioned configuration, the thickness of an outer layer (the flexible sheath and the reinforcing material) in a particular direction about the axis line is larger than that of another direction about the axis line. Therefore, excellent twisting response and resilience can be achieved in regard to a flexible tube for an endoscope employing framed structure unit in which a plurality of joint members are rotatably coupled to each other to enhance durability against autoclaving.

BRIEF DESCRIPTION OF THE ACCOMPANYING DRAWINGS

DETAILED DESCRIPTION OF THE EMBODIMENTS

Hereinafter, embodiments according to the invention are described with reference to the accompanying drawings.

First Embodiment

Figure 2:
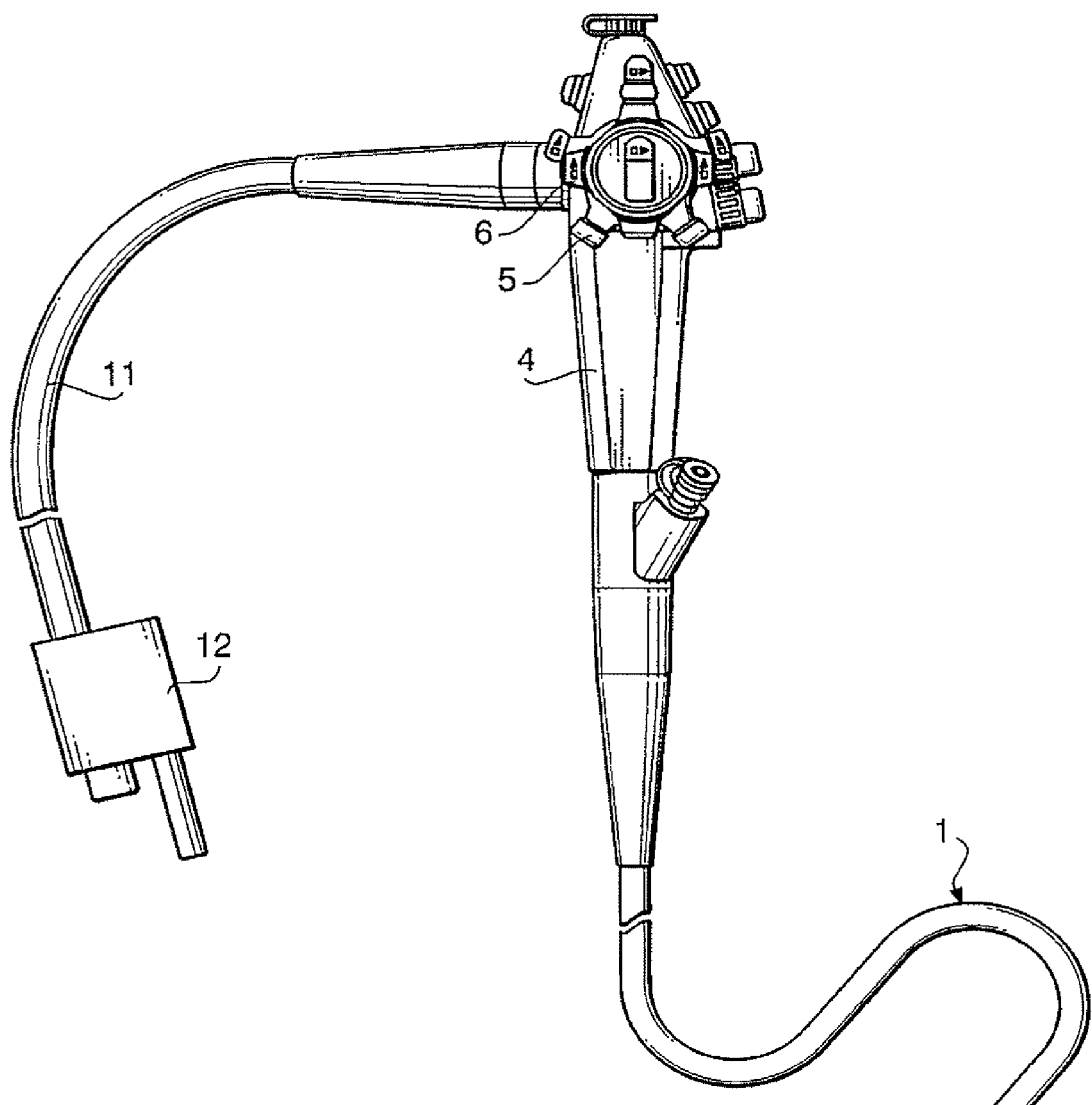
FIG. 2 shows an outer appearance of an endoscope having the flexible tube according to a first embodiment of the invention.

FIG. 2 shows an outer appearance of an endoscope having a flexible tube 1 according to a first embodiment of the invention. The flexible tube 1 to be inserted into a body cavity has flexibility of being able to be bent freely by an external force. The flexible tube 1 is configured such that internal components such as an optical fiber, signal cables and tubes (not shown) are provided in inner space of the flexible tube 1 throughout the length of the flexible tube 1.

At a tip portion of the flexible tube 1, a bendable portion 2 which can be bent by a remote control is provided. A tip body unit 3 having an observation window is attached at a tip of the flexible tube 1. An operation unit 4 is provided at a proximal end portion of the flexible tube 1. By selectively operating knobs 5 and 6 on the operation unit 4 connected to the proximal end of the flexible tube 1, an operator is able to bend the bendable portion 2 freely as indicated by a chain double dashed line in FIG. 1.

Figure 1:
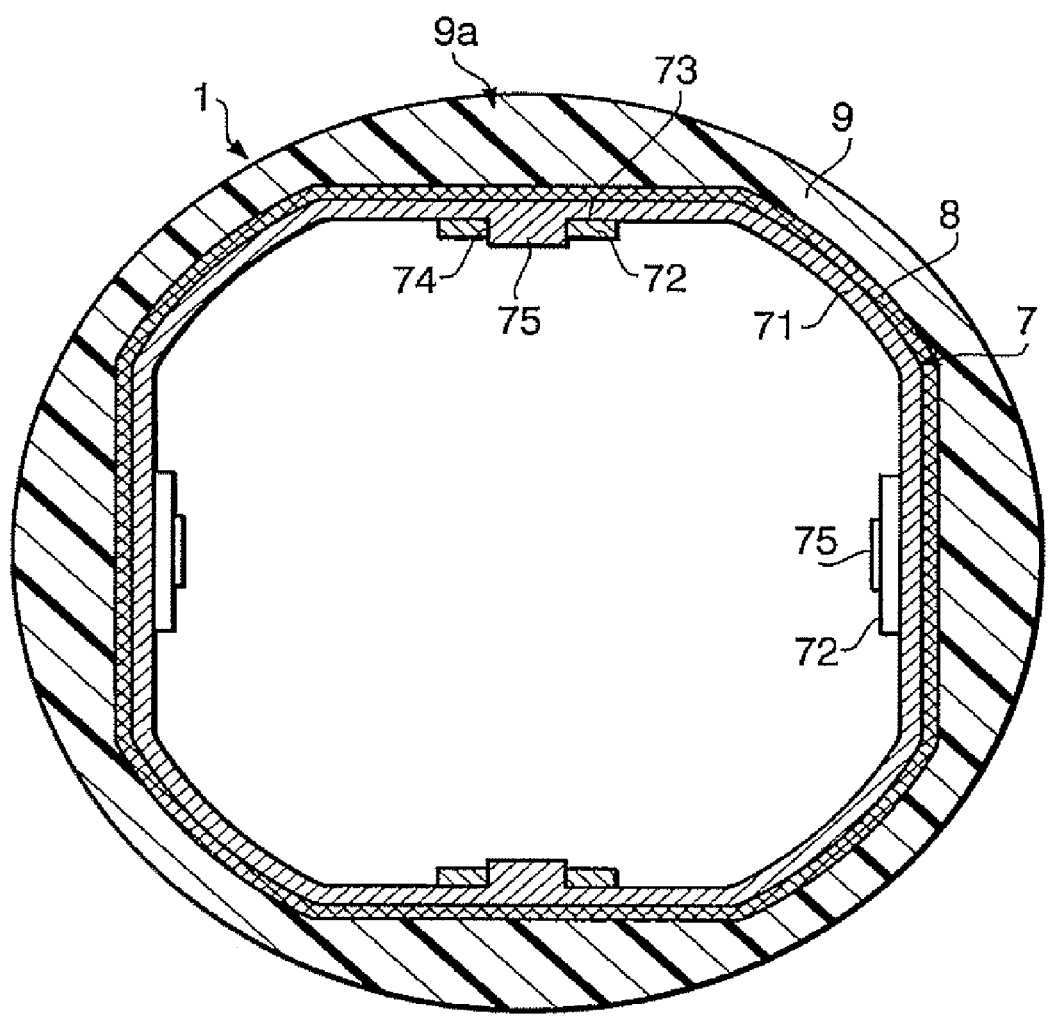
FIG. 1 is a cross section of a flexible tube along a line I-I in FIG. 3.
Figure 3:
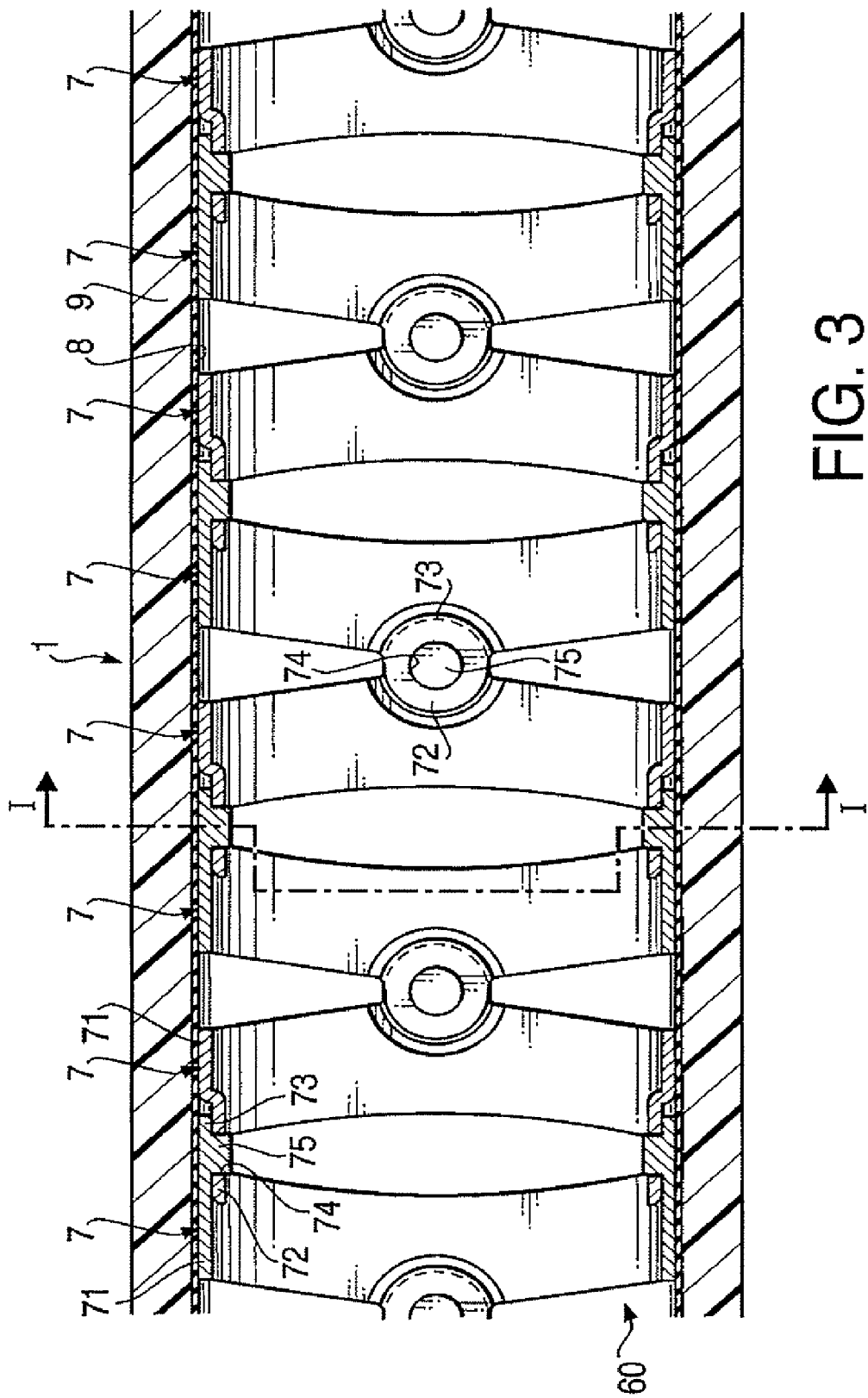
FIG. 3 shows an internal structure of the flexible tube.

FIG. 3 shows an internal structure of the flexible tube 1. FIG. 1 is a cross section of the flexible tube 1 along a line I-I in FIG. 3. As shown in FIG. 3, the flexible tube 1 includes a framed structure unit 60 configured to be bent freely. Specifically, the framed structure unit 60 includes a plurality of joint members 7 rotatably attached to each other. Each of the joint members 7 has rigidity and has a form of short cylinder. The framed structure unit 60 is covered with a reticulated tube 8 reticulated with, for example, very fine thread made of stainless steel. The outermost layer of the flexible tube 1 is a flexible sheath 9. The flexible sheath 9 is made of synthetic resin or elastomer. The flexible sheath 9 is formed by extrusion molding to cover the reticulated tube 8. In FIGS. 1 and 3, the internal components are not shown for the sake of simplicity.

Figure 4:
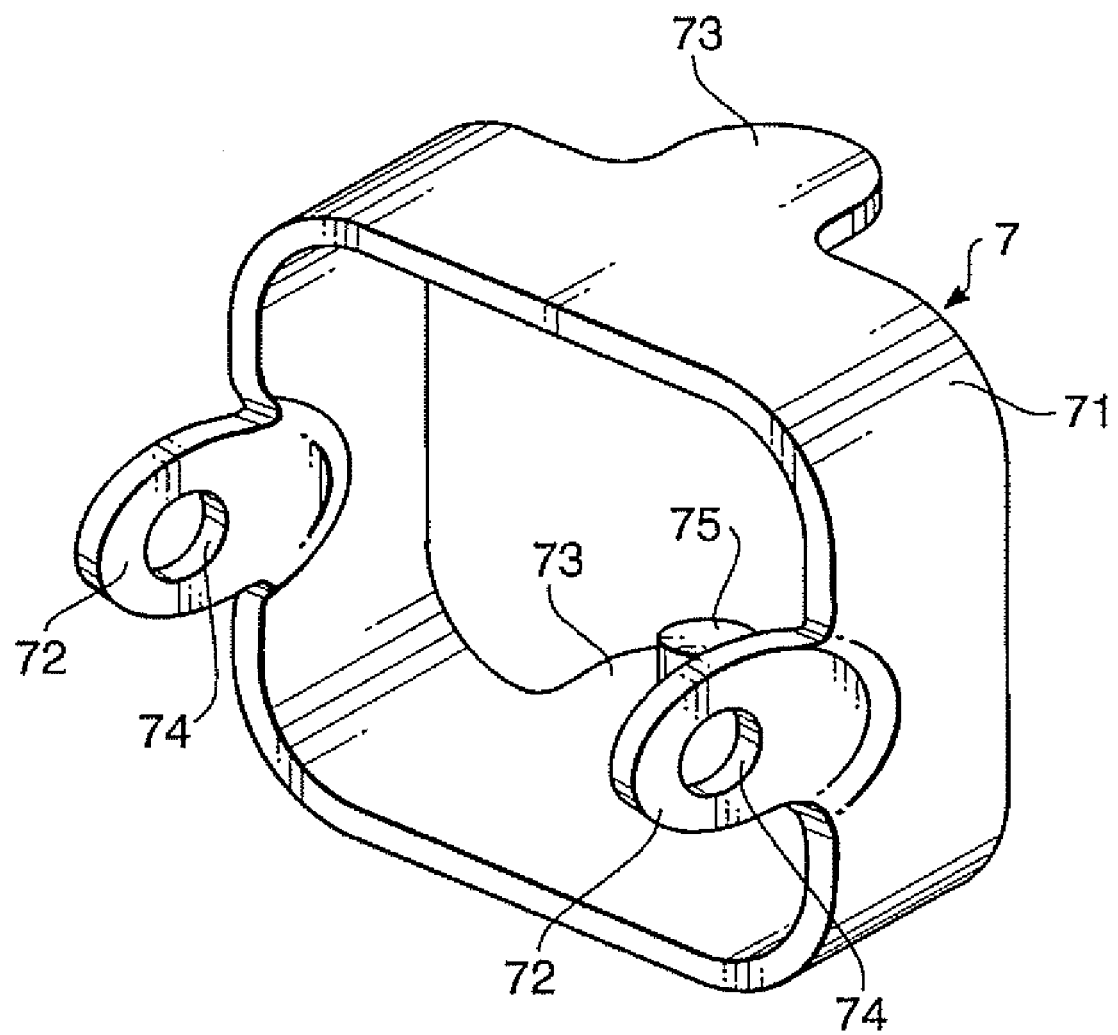
FIG. 4 is a perspective view of a joint member provided in the flexible tube.

FIG. 4 is a perspective view of the joint member 7. The joint member 7 is made of, for example, austenitic stainless steel, and is formed to be a short tube having a rectangular sectional shape. Specifically, the joint member 7 may be formed by crushing a short cylinder at positions 90° apart in angle with respect to each other about an axis line.

As shown in FIG. 4, the joint member 7 includes a short tube unit 71. A pair of tabs 72 and 72 is formed to protrude from a front edge of the short tube unit 71. A pair of tabs 73 and 73 is formed to protrude from a rear edge of the short tube unit 71. The tabs 72 and 72 are formed at opposed sides of the short tube unit 71, and the tabs 73 and 73 are formed at opposed sides of the short tube unit 71.

The tabs 72 and 72 have holes 74 and 74, respectively. The tabs 73 and 73 are provided with connecting shafts 75 and 75 respectively protruding inwardly from inside surfaces of the tabs 73 and 73. The connecting shafts 75 and 75 of one joint member 7 are inserted into holes 74 and 74 of the tabs 72 and 72 of a neighboring joint member 7 from the outside toward the inside so that the connecting shafts 75 and 75 rotatably fit into the holes 74 and 74. As shown in FIG. 4, the holes 74 and 74 are located at positions 90° apart from corresponding connecting shafts 75 and 75 about a center axis of the joint member 7.

As shown in FIGS. 1 and 3, the tab 73 on which the connecting shaft 75 is formed is configured to form a common surface with the short tube unit 71 and to have the same thickness as that of the short tube unit 71. The tab 72 in which the hole 74 is formed is recessed from an outer surface of the short tube unit 71 so that the height of an outer surface of the tab 72 from the center axis is equal to the height of an inner surface of the short tube unit 71 from the center axis.

As shown in FIG. 1, the outer surface of the flexible sheath 9 is formed to have a circular cross section. On the other hand, the joint member 7 is formed such that a short cylinder is crushed at positions 90° apart in angle with respect to each other about the axis line. Therefore, parts (heavy wall thickness parts 9a) of the flexible sheath 9 located outside the flat parts of the joint member 7 have the wall thickness larger than those of the other parts of the flexible sheath 9. The flexible tube 1 is configured to have the cross section shown in FIG. 1 throughout its length.

Such a configuration enables the flexible tube 1 to have a high degree of twisting response, representing rotating motion of a tip portion of the flexible tube 1 in response to an operation to rotate a proximal portion of the flexible tube 1 about an axis line, and a high degree of resilience, representing motion of the flexible tube 1 getting back to a straightened state after being bent by an external force. As a result, usability of the endoscope can be enhanced.

It is possible to increase the twisting response and the resilience by forming the flexible tube 1 such that the entire part of the flexible sheath 9 is formed to have a heavy thickness. However, in this case the inner space of the flexible tube 1 becomes narrow. Consequently, the number of internal components that the flexible tube 1 is able to accommodate decreases, and thereby the performance as an endoscope is deteriorated.

By contrast, according to the embodiment, the joint member 7 is configured such that each of the sides thereof at which the tabs 72 and 73 are located, is formed to be a flat shape. In general, a flexible tube is configured such that space in the vicinity of the flat-shape parts of each joint member in the internal space of the flexible tube is used as dead space.

Therefore, according to the embodiment, it is possible to enhance the twisting response and resilience without decreasing available internal space for the internal components in the flexible tube 1.

However, the outer shape of the cross section of the joint member 7 may be different from the above mentioned rectangular shape. That is, the joint member 7 may be configured such that the outer shape of the cross section thereof is a non-circular shape so that the thickness of the flexible sheath 9 in a particular direction about the axis line is larger than that of another direction about the axis line.

Second Embodiment

Figure 5:
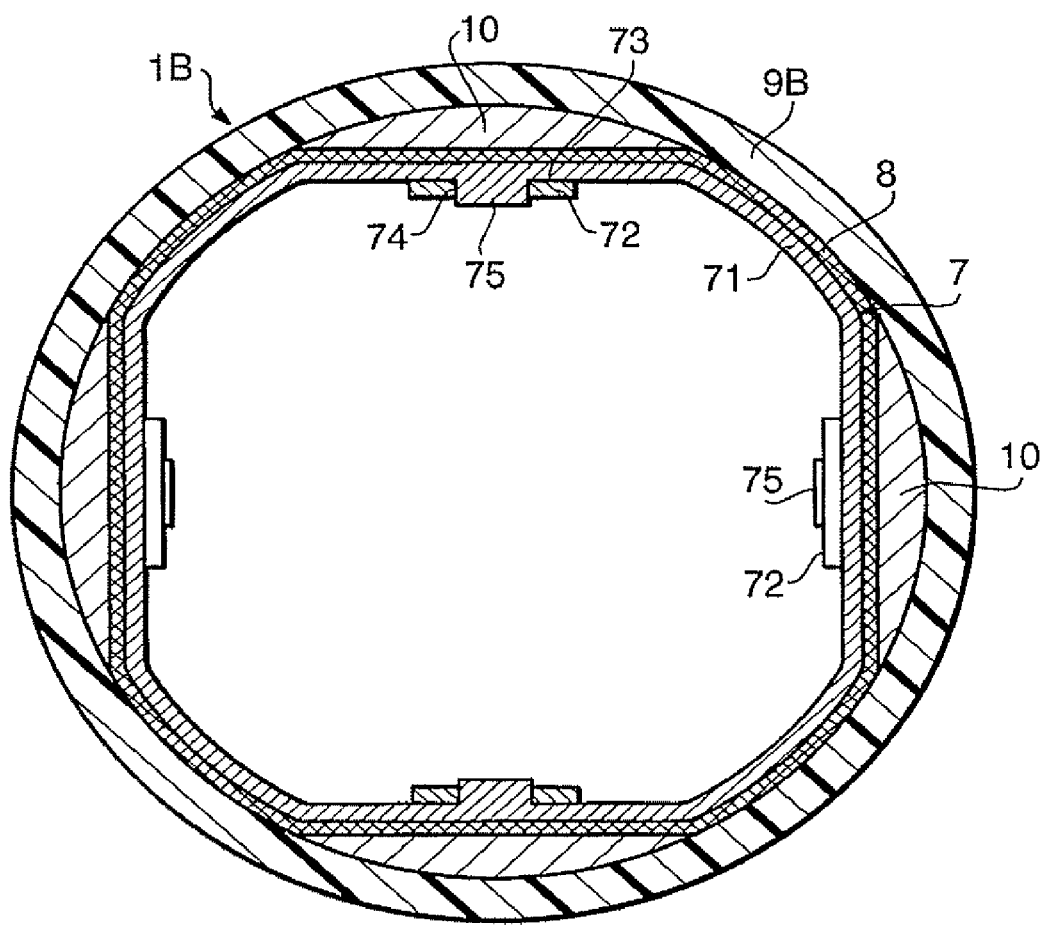
FIG. 5 shows a cross section of a flexible tube according to a second embodiment.

Hereafter, a flexible tube 1B according to a second embodiment is described. The flexible tube 1B can be employed in the endoscope shown in FIG. 2 in place of the flexible tube 1. FIG. 5 shows a cross section of the flexible tube 1B. In FIG. 5, to elements which are substantially the same as those of the first embodiment, the same reference numbers are assigned, and explanations thereof will not be repeated.

Similarly to the flexible tube 1 according to the first embodiment, the flexible tube 1B is configured such that the joint member 7 is covered with the reticulated tube 8, and the reticulated tube 8 is covered with a flexible sheath 9B. An outer surface of the flexible sheath 9B is circular in cross section. In space formed outside the flat parts of the joint member 7, reinforcing material 10 made of superelastic steel is provided. That is, the space in which the reinforcing material 10 is provided is located at a portion where a distance between the outer surface of the flexible sheath 9B and the outer surface of each joint member 7 is larger than that of another portion in a circumferential direction of the flexible tube 1B. That is, the flexible sheath 9B does not have thicker parts in contrast to the first embodiment.

The flexible tube 1B is provided with the reinforcing material 10 throughout its length. Such a configuration makes it possible to further enhance the twisting response and resilience of the flexible tube 1B.

In FIG. 5, the reinforcing material 10 is provided between the flexible sheath 9B and the reticulated tube 8. However, the flexible tube 1B may be configured such that the reinforcing material 10 is provided between the reticulated tube 8 and the joint member 7.

Third Embodiment

Figure 6:
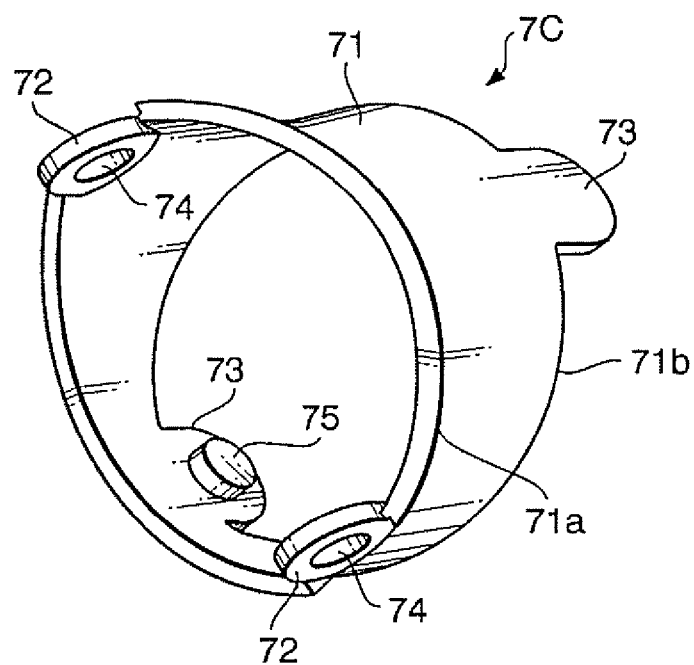
FIG. 6 is a perspective view of a joint member according to a third embodiment.

Hereafter, a joint member 7C according to a third embodiment is described. The joint member 7C can be employed in the above mentioned flexible tubes shown in FIGS. 1 and 5 in place of the joint member 7. FIG. 6 is a perspective view of the joint member 7C. In FIG. 6, to elements which are substantially the same as those of the first embodiment, the same reference numbers are assigned, and explanations thereof will not be repeated.

The joint member 7C is configured to have such a form that a circular short cylinder is crushed on the side of an end portion 71a to have an elliptical shape and is crushed on the side of an end portion 71b to have an elliptical shape having a direction of a major axis perpendicularly crossing a direction of a major axis of the elliptical shape formed at the end portion 71a, A cross section of an intermediate part of the circular short cylinder is formed to be a circular shape.

Figure 7:
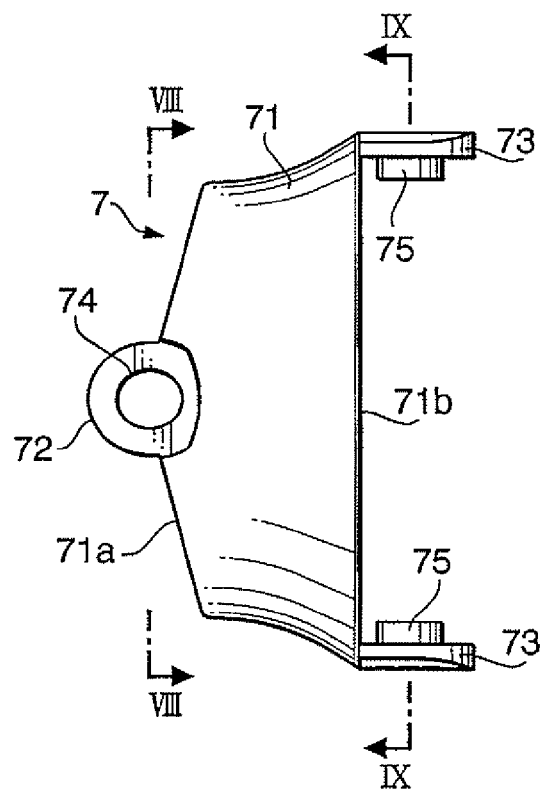
FIG. 7 is a side view of the joint member shown in FIG. 6.
Figure 8:
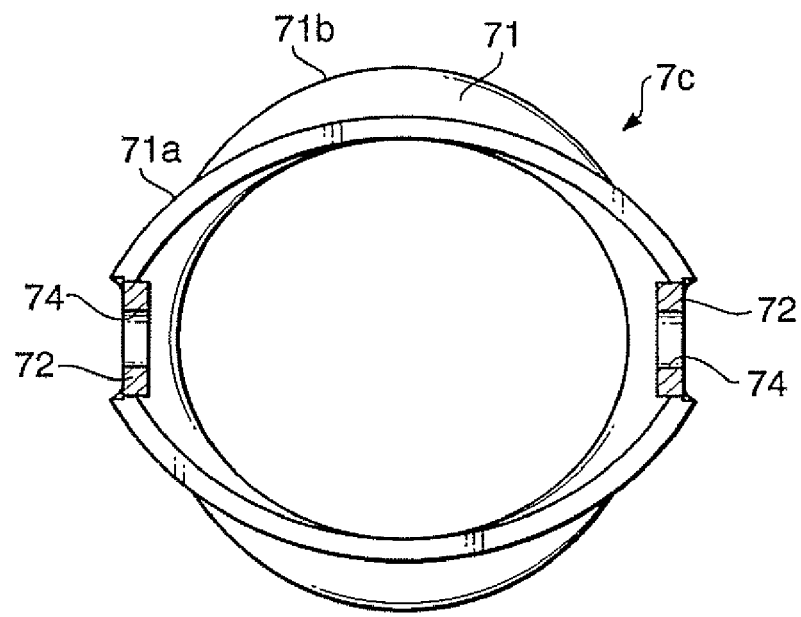
FIG. 8 is a cross section of the joint member along a line VIII-VIII in FIG. 7.
Figure 9:
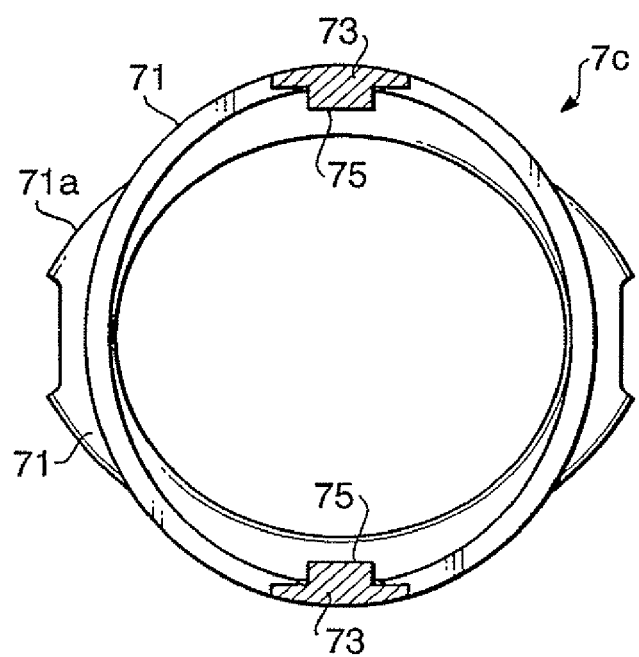
FIG. 9 is a cross section of the joint member along a line IX-IX shown in FIG. 7.

FIG. 7 is a side view of the joint member 7C. FIG. 8 is a cross section of the joint member 7C along a line VIII-VIII in FIG. 7, and FIG. 9 is a cross section of the joint member 7C along a line IX-IX shown in FIG. 7. As shown in FIGS. 6 to 9, the pair of tabs 72 having the holes 74 is formed at major axis edges of the elliptical shape formed at the end portion 71a, and the pair of tabs 73 having the connecting shafts 75 is formed at major axis edges of the elliptical shape formed at the end portion 71b.

Figure 10:
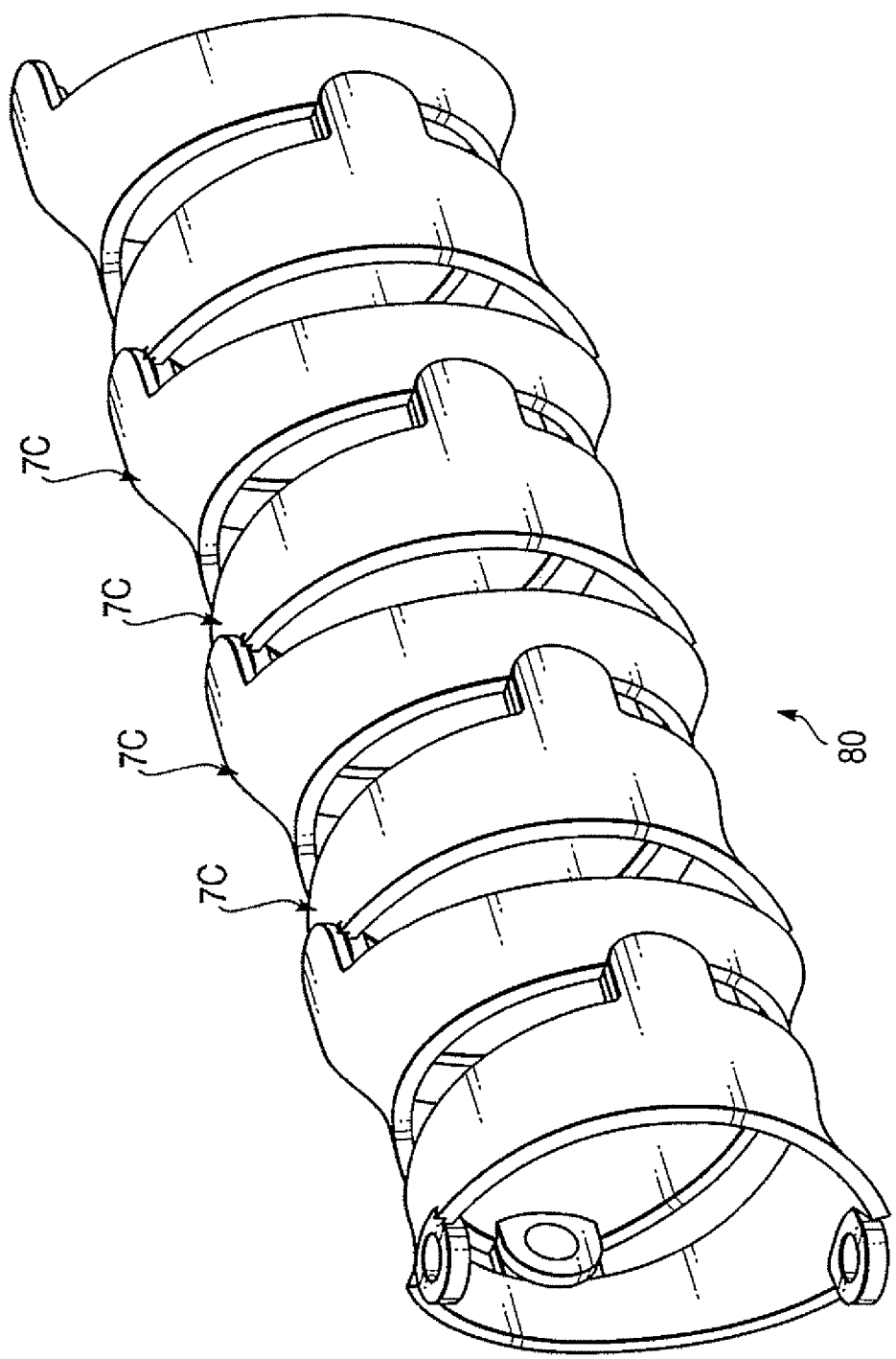
FIG. 10 is a perspective view of a framed structure unit according to the third embodiment.

FIG. 10 is a perspective view of a framed structure unit 80 in which a plurality of joint members 7C are connected to each other by rotatably coupling the connecting shafts 75 and the holes 74 of the neighboring joint members with respect to each other. By this configuration, the framed structure unit 80 is able to bend freely.

Similarly to the first embodiment, a reticulated tube reticulated with, for example, very fine thread made of stainless steel is formed to cover the outer surface of the framed structure unit 80. As an outermost layer, a flexible sheath made of synthetic resin or elastomer is formed by extrusion molding to cover the reticulated tube. A flexible tube for an endoscope is thus configured.

As described above, according to the above mentioned embodiments, the thickness of the flexible sheath (or an outer layer) in a particular direction about the axis line is larger than that of another direction about the axis line. Therefore, excellent twisting response and resilience can be achieved in regard to a flexible tube for an endoscope employing framed structure unit in which a plurality of joint members are rotatably coupled to each other to enhance durability against autoclaving.

Although the present invention has been described in considerable detail with reference to certain preferred embodiments thereof, other embodiments are possible.

For example, joint members are rotatably coupled to each other with rivets. The joint member 7 may be configured to have a non-circular cross section such as a polygonal shape (e.g., a triangular shape, a pentagonal shape, and etc.). Connecting parts (i.e., tabs having the connecting shafts or the holes) may be located at positions other than the flat parts of the joint member.

This application claims priority of Japanese Patent Applications No. P2006-002384, filed on Jan. 10, 2006, and No. P2006-285835, filed on Oct. 20, 2006. The entire subject matters of the applications are incorporated herein by reference.

What is claimed is:

1. An endoscope including a flexible tube, the flexible tube comprising:

a framed structure unit having a plurality of joint members rotatably coupled to each other so that the framed structure unit is able to bend freely, each joint member having a cylindrical shape;

a reticulated tube that is reticulated with thread and covers the framed structure unit; and a flexible sheath that has flexibility and covers the reticulated tube;

wherein:

a cross section of an outer surface of the flexible sheath has a circular shape;

a cross section of an outer surface of each joint member has a non-circular shape so that a wall thickness of the flexible sheath has a part that is thicker in a particular direction about an axis line of the flexible tube than another part of the wall thickness of the flexible sheath;

the cylindrical shape of each joint member is configured to have a first elliptical cross section at a first end portion and a second elliptical cross section at a second end portion, a major axis of the first elliptical cross section at the first end portion being perpendicular to a major axis of the second elliptical cross section at the second end portion; and a pair of tabs, each having a hole, are provided at ends of the major axis of the first elliptical cross section at the first end portion.

2. The flexible tube according to claim 1, wherein the flexible tube is formed by extrusion molding.

3. The flexible tube according to claim 1, wherein a pair of tabs each having a connecting shaft is provided at ends of the major axis of the elliptical cross section of the second end portion.

4. The flexible tube according to claim 1, wherein major and minor axes of the first elliptical cross section and of the second elliptical cross section lie in planes that are parallel to each other and transverse to a longitudinal of the cylindrical shape.

5. An endoscope including a flexible tube, the flexible tube comprising:

a framed structure unit having a plurality of joint members rotatably coupled to each other so that the framed structure unit is able to bend freely, each joint member having a cylindrical shape;

wherein:
the cylindrical shape of each joint member is configured to have a first elliptical cross section at a first end portion and a second elliptical cross section at a second end portion, a major axis of the first elliptical cross section at the first end portion being perpendicular to a major axis of the second elliptical cross section at the second end portion; and
a pair of tabs, each having a hole, are provided at ends of the major axis of the first elliptical cross section at the first end portion.

6. The flexible tube according to claim 5, wherein a pair of tabs each having a connecting shaft is provided at ends of the major axis of the elliptical cross section of the second end portion.

7. The flexible tube according to claim 5, further comprising a reticulated tube that covers the framed structure unit.

8. The flexible tube according to claim 7, further comprising a flexible sheath that covers the reticulated tube.

9. The flexible tube according to claim 5, wherein major and minor axes of the first elliptical cross section and of the second elliptical cross section lie in planes that are parallel to each other and transverse to a longitudinal of the cylindrical shape.

* * * * *